United States Patent [19]

Giobbio et al.

[11] 4,347,247

[45] Aug. 31, 1982

[54] PHARMACOLOGICAL PREPARATION COMPOSED OF A QUINOXALINE DERIVATIVE MIXED WITH SODIUM BICARBONATE

[75] Inventors: Vincenzo Giobbio, Turin; Livio Buracchi, Ivrea, both of Italy

[73] Assignee: Pierrel S.p.A., Milan, Italy

[21] Appl. No.: 145,811

[22] Filed: May 1, 1980

[30] Foreign Application Priority Data

May 7, 1979 [IT] Italy .................. 67949 A/79

[51] Int. Cl.³ .................................. A61K 31/495
[52] U.S. Cl. ............................... 424/250; 424/2
[58] Field of Search .............. 544/353, 355; 424/2, 424/250; 252/7

[56] References Cited

U.S. PATENT DOCUMENTS 3,948,911 4/1976 McFarland ................. 544/355
4,006,142 2/1977 Kuhla ........................ 544/353

OTHER PUBLICATIONS

Chem. Abst. 9th Collect. Index, (1972–1976), p. 10088cs.
Beumer–Chem. Abst., vol. 90, (1979), p. 150381x.

*Primary Examiner*—Sam Rosen
*Attorney, Agent, or Firm*—Young & Thompson

[57] ABSTRACT

A pharmacological preparation for use in animal husbandry, consists essentially of sodium bicarbonate and an active ingredient which is either 2-methyl-3 (β-hydroxyethylcarbamoyl) quinoxaline-1,4-di-N-oxide or $N_1$, $N_4$-dioxo-quinoxaline-2-methyleneimino-N-methylurethane. The sodium bicarbonate imparts fireproofness to what would otherwise be a highly flammable preparation.

3 Claims, No Drawings

PHARMACOLOGICAL PREPARATION COMPOSED OF A QUINOXALINE DERIVATIVE MIXED WITH SODIUM BICARBONATE

The present invention relates to a product obtained by conditioning and supporting a quinoxaline derivative, known for its pharmacological activity and for its use in the field of animal husbandry, with sodium bicarbonate.

The said conditioning and support are extremely useful inasmuch as they make it easy to handle, mix and store a substance which is otherwise very dangerous in that it is unstable, highly flammable and also explosive.

The product supported according to the invention can be marketed, and the end-user can further mix it with animal feed in the required proportions with absolutely no risk of flammability.

The quinoxaline derivatives currently used in animal husbandry are of two types and their structure is similar. They are 2-methyl-3($\beta$-hydroxyethylcarbamoyl)-quinoxaline1,4-di-N-oxide and $N_1,N_4$-dioxo-quinoxaline-2-methyleneimino-N-methylurethane.

Their structural formulas are as follows:

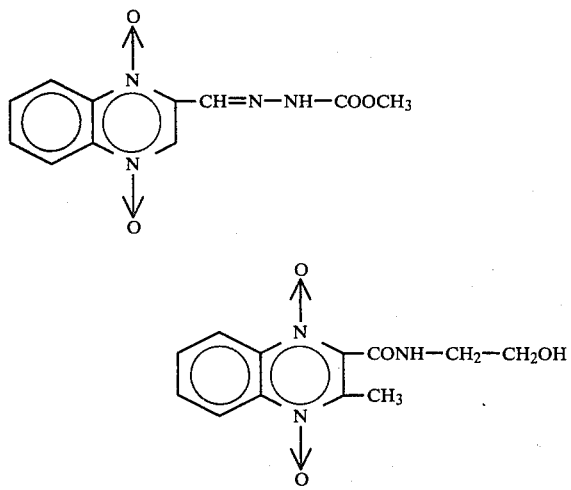

These two substances are also similar pharmacologically: they possess particular chemotherapeutic properties which make them effective urinary tract antiseptics, but are also systemic disinfectant agents, combat chronic respiratory diseases in poultry, certain bacterial infections in pigs and are particularly effective as animal feed supplements and are thus useful as animal growth promoters. However, the major disadvantage of these two substances, resulting from their labile chemical structure, is their high flammability.

To overcome this serious problem, the present invention proposes to mix the quinoxaline derivative to be employed with sodium bicarbonate in a 50% proportion, or also in other proportions in the range 20:80. This addition of sodium bicarbonate to the quinoxaline derivative decreases or, if the proportion of sodium bicarbonate added is at least 50%, totally eliminates all risk of fire due to friction, impact or any other cause, thus allowing these quinoxaline derivatives to be handled with absolute safety.

When either of these otherwise highly flammable substances is mixed in equal parts with sodium bicarbonate it will no longer catch fire even if primed with a naked flame. The antifire properties of sodium bicarbonate, already known in other fields, are thus in the present instance absolutely decisive, more exactly because sodium bicarbonate is a support which effects a chemical mediation of particular efficacy for the purpose in question as a result of the evolution of carbon dioxide resulting from the known reaction:

$$2NaHCO_3 \rightarrow Na_2CO_3 + CO_2 + H_2O$$

These concepts find endorsement in various laboratory trials which aimed to identify the substance or substances most suitable for the purpose in question, but which at the same time took all due account of the fact that the selected additive must be compatible with the two quinoxaline derivatives as regards chemical interaction and pH. Selection of the most suitable substance was also conditioned by the fact that, as well as requiring to be an antifire and stabilizing agent, it will be ingested by animals for long periods, even if in small doses, and must therefore be nontoxic. The trials mentioned showed that sodium bicarbonate is the most effective and least toxic substance available for the purpose. It is a nontoxic substance.

Moreover, it has the further advantage of allowing a readier digestibility of the two quinoxaline derivatives.

The quantitative ratio of the two components of the mixture, i.e. the quinoxaline derivative and sodium bicarbonate, can therefore be 50:50, or in a range of between 80% of one component and 20% of the other, though it is more advisable to use 50% or more sodium bicarbonate.

The mixing of the two components can be carried out in the quinoxaline synthesis reactor, at the end of the reaction, when the sodium bicarbonate can be added in the desired ratio so as to protect the quinoxaline in the subsequent steps of isolation, centrifugation, drying and grinding.

The following example, which is not limiting as regards other types of mixing, is illustrative of the kind mentioned.

EXAMPLE

To a reaction flask containing 100 g of 2-methyl-3($\beta$-hydroxyethylcarbamoyl)quinoxaline1,4-di-N-oxide, and in the presence of the reaction solvent, addition was made of 100 g of sodium bicarbonate. The whole was vacuum filtered and transferred to a vacuum dryer. 200 g of 2-methyl-3-($\beta$-hydroxyethylcarbamoyl)quinoxaline1,4-di-N-oxide containing 50% sodium bicarbonate was obtained. Even if primed with a naked flame, this mixture was non-flammable and did not decompose.

We claim:

1. A pharmaceutical composition for use in animal husbandry, consisting essentially of sodium bicarbonate and a quinoxaline derivative selected group the group consisting of 2-methyl-3($\beta$-hydroxyethylcarbamoyl)-quinoxaline-1,4-di-N-oxide and $N_1,N_4$-dioxo-quinoxaline-2-methyleneimino-N-methylurethane, the sodium bicarbonate and said derivative being admixed in a weight ratio of at least 50% sodium bicarbonate.

2. A composition as claimed in claim 1, in which said derivative is 2-methyl-3($\beta$-hydroxyethylcarbamoyl)-quinoxaline-1,4-di-N-oxide.

3. A composition as claimed in claim 1, in which said derivative is $N_1,N_4$-dioxo-quinoxaline-2-methyleneimino-N-methylurethane.

* * * * *